United States Patent
Ahn

[11] Patent Number: 5,527,355
[45] Date of Patent: Jun. 18, 1996

[54] APPARATUS AND METHOD FOR PERFORMING ANEURYSM REPAIR

[76] Inventor: Sam S. Ahn, 100 UCLA Medical Plaza, Suite 510, Los Angeles, Calif. 90024

[21] Appl. No.: 300,059

[22] Filed: Sep. 2, 1994

[51] Int. Cl.⁶ .................................................. A61F 2/06
[52] U.S. Cl. ................................ 623/1; 623/11; 623/12
[58] Field of Search ........................... 623/1, 2, 11, 12, 623/66; 606/108, 151, 153, 191, 194

[56] References Cited

U.S. PATENT DOCUMENTS

| | | | |
|---|---|---|---|
| 3,789,828 | 2/1974 | Schulte | 623/66 |
| 4,140,126 | 2/1979 | Choudhury . | |
| 4,190,909 | 3/1980 | Ablaza | 623/1 |
| 4,787,899 | 11/1988 | Lazarus . | |
| 5,084,065 | 1/1992 | Weldon et al. | 623/1 |
| 5,104,399 | 4/1992 | Lazarus . | |
| 5,219,355 | 6/1993 | Parodi et al. . | |
| 5,330,490 | 7/1994 | Wilk et al. | 606/153 |

FOREIGN PATENT DOCUMENTS

| | | | |
|---|---|---|---|
| 617930 | 10/1994 | European Pat. Off. | 623/1 |
| 2269104 | 2/1994 | United Kingdom | 623/1 |

*Primary Examiner*—David H. Willse
*Assistant Examiner*—P. Zuttarelli
*Attorney, Agent, or Firm*—Blakely, Sokoloff, Taylor, Zafman

[57] ABSTRACT

The present invention is an apparatus and method of treating an aneurysm by applying to an aneurytic blood vessel a band around its exterior surface, at the position where the attachment system of the graft attaches the graft to the vessel. The band can be in the form of a strap with an attachment means such a Velcro®, or a clasp, or it can be heat sealed onto the vessel or sewn thereon.

17 Claims, 3 Drawing Sheets

APPARATUS AND METHOD FOR PERFORMING ANEURYSM REPAIR

BACKGROUND OF THE INVENTION

1. Field of the Invention

This invention relates to the field of vascular surgery, and more specifically, is directed to an apparatus and method for repairing a vascular aneurysm.

3. Art Background

The prior art method of treating a vascular aneurysm and some other vascular problems has been to excise the aneurytic tissue and replace it with a synthetic graft or a graft from another section of the body. This surgery has been extremely risky, and a high mortality rate has been observed, primarily because the condition of the patients undergoing the surgery is generally weak.

In recent years, a number of companies have devised new methods and devices for treating aneurysms and other vascular disease in which the blood vessels are damaged and unable to safely retain the blood passing therethrough. The devices are comprised of vascular prosthetic graft with a connecting means of some type for connecting the prosthesis to the damaged blood vessel at a position displaced from the aneurysm or damage, the prosthesis being sized to fit within the blood vessel, so that the graft permits the blood to travel through the damaged vessel without applying any pressure to the damaged vessel at the point of damage.

U.S. Pat. No. 4,140,126 discloses one such prior art device and method for repairing an aneurysm. This device is positioned in a vessel in a collapsed form, and is then expanded and then attached to the inside of the wall of the vessel with hooks which extend when the device is expanded from its collapsed form.

U.S. Pat. No. 4,787,899 discloses an artificial intraluminal graft with u-shaped staples near the end for securing the graft to the vessel. U.S. Pat. No. 5,104,399, which is a continuation in part of the '899 patent, discloses a generally cylindrical graft with a staple assembly in a v-shaped lattice work which is assembled into its operational configuration by the inflation of a balloon in the interior of the assembly.

U.S. Pat. No. 5,219,355 discloses an intraluminal prosthesis for repairing aneurysms which utilizes a catheter having two inflatable balloons, one near each end of the prosthesis, for securing the prosthesis in place in the vessel.

While the retention systems appear to be effective in retaining the grafts in the vessel, over time, it is anticipated, and there have been some recent reports that the vessel wall where the graft connects thereto becomes weakened, and a subsequent aneurysm may occur at that position. As an additional factor, the penetration into the wall by the staples causes some fibrosis, and the tissue buildup at the location of the connection can cause some blood flow restriction which would increase the pressure on the vessel walls at the site of contact between the blood vessel and the graft. This condition may also increase the risk of a subsequent aneurysm.

The present invention is designed to operate in conjunction with a number of various retention systems for retaining a vascular graft in a vessel by attaching the graft to the interior wall of the vessel, without the risk. Each of these has certain deficiencies which are described below, which deficiencies are resolved by the present invention.

SUMMARY OF THE INVENTION

A method and apparatus are disclosed which overcome the disadvantages and limitations associated with the prior art devices, and which can be used in conjunction with the prior art system to ensure that the vessel retention system of a vascular graft functions without causing certain complications. More specifically, the complications, which may occur over time, relate to a weakening of the wall of the blood vessel at the attachment site of the graft to the vessel, causing an aneurysm at the new location, typically upstream, but possibly downstream from the original aneurytic site. The secondary aneurysm is the result of the weakening of the wall of the blood vessel due to the use of staples to attach the graft to the vessel, and various other factors.

The present invention is an apparatus and method of alleviating this problem by applying to the blood vessel a band around its exterior surface, at the position where the attachment system of the graft attaches the graft to the vessel. The band can be in the form of a strap with an attachment means such a Velcro®, or a clasp, or it can be heat sealed onto the vessel or sewn thereon. The band can be applied laparoscopically or using direct field of vision. Typically in the application of the graft it is inserted in the blood vessel downstream from the aneurysm and then advanced to the site of the aneurysm through the interior of the vessel, and then expanded into its full radial size and secured in place using the retention system designed for it, of the different systems known in the art. The position of the graft can be confirmed using x-ray or other imaging technique. Once the graft is in place and assembled and secured in place with its retention system, the band can be applied to the exterior of the blood vessel. The length of the band can vary, but should be at least long enough to envelope the entire length of the blood vessel to which the graft is attached at the attachment site.

BRIEF DESCRIPTION OF THE DRAWINGS

The objects of the present invention will be described with respect to the following figures in which.

DETAILED DESCRIPTION OF THE INVENTION

An apparatus is described for securing on a blood vessel a vascular graft containing a retention system. A method of securing the vascular graft is also described. Renal arteries extend from the abdominal aorta and the arteries are divided into the common iliac artery at the lower most end. The aorta is a major blood vessel of the body and is characterized by generally healthy tissue. However, one section of the aorta is damaged, and this is where a large aneurysm has formed characterized by a bulge in the wall of the aorta. If the aneurysm is not repaired or otherwise treated in time it will eventually rupture causing a fatal hemorrhage within a short period of time. It will be understood by persons of skill in the art that while the present invention is described with reference to an aneurysm in the aorta, the present invention will be useful in the treatment of aneurysm in other vessels as well, the usefulness of the vascular graft technology in the repair of aneurysm being generally known in the art.

The present invention is an adjunct to a prosthetic graft for repairing the damaged blood vessel. The prosthetic graft is primarily made of generally biologically acceptable material, such as Dacron, Nylon, Gortex, and the like. The graft is an elongated tube of the material and a retention systems for retaining the graft within the blood vessel. The retention system is comprised of a cylindrical array of staples which have outward protruding barbs. The retention system is expandable and collapsible, which is presently necessary and consistent with the method of implantation in which the graft is installed in a blood vessel at a site remote from the aneurysm, and is then pushed and guided up to the aneurytic site, and then installed in place in the blood vessel.

Figure 1:
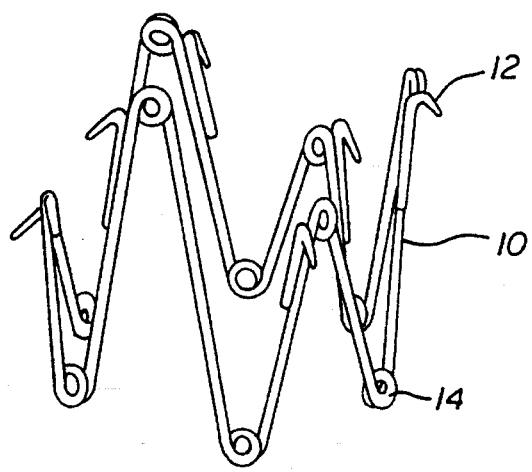
FIG. 1 is an illustration of one type of prior art graft retention system.
Figure 2:
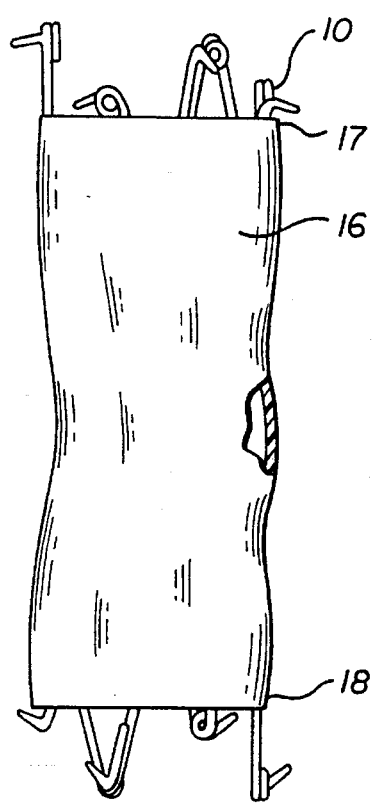
FIG. 2 is a partially cutaway view of a prior art graft with a retention system.

FIG. 1 is an illustration of one prior art graft retention system in which the staples are collapsible and expandable. The graft retention system 10 comprises a plurality of staples or barbs 12 extending outward, and connected together in a v-shaped network with a spring hinge 14 interconnecting each staple. It will be appreciated by persons of skill in the art that there are a number of different graft retention systems, including a variety of different staple configurations and balloon retention systems, and the present invention will work with any of these systems. As shown in FIG. 2, the graft retention system of FIG. 1 is disposed within the vascular graft 16, shown in a partially cutaway view, with the retention system 10 being partially viewable above and below the edges 17 and 18 of the graft. The graft retention system 10 is retained in the graft by any suitable means.

Figure 3:
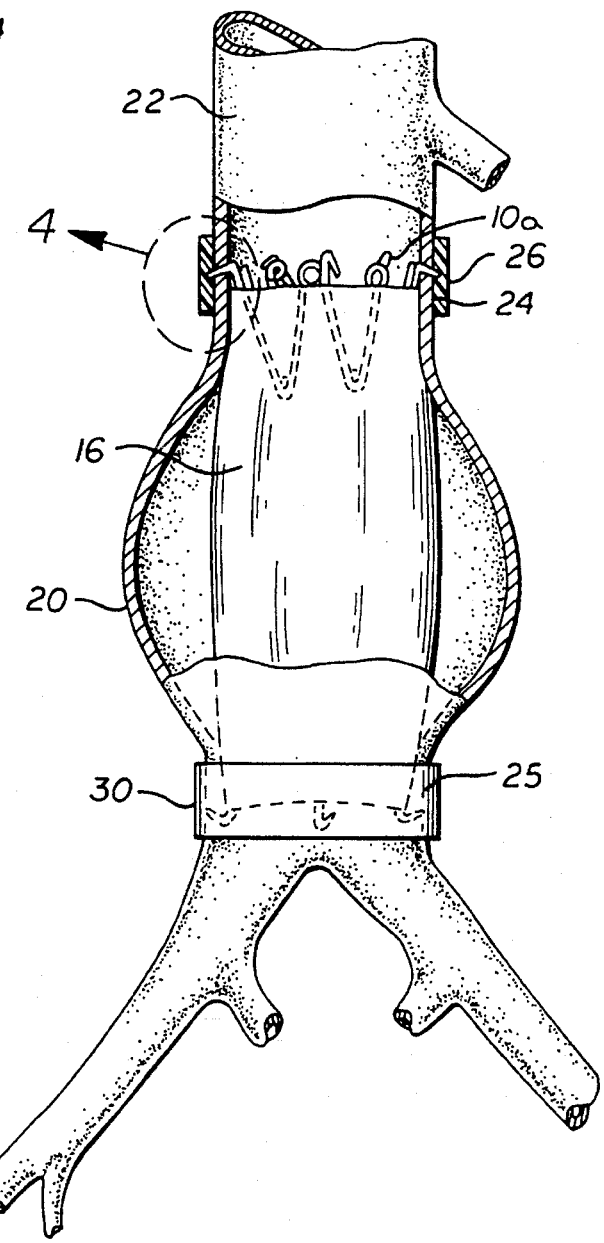
FIG. 3 is a partial sectional view of an aneurytic blood vessel with a vascular graft disposed therein, and the band of the present invention disposed around the blood vessel at the site where the retention system engages the blood vessel.

FIG. 3 illustrates the present invention which is a band disposed around the exterior of the blood vessel at the location where the retention system is connected to the blood vessel remote from the actual position of the aneurysm. More specifically, the graft 16 is disposed at the cite of the aneurysm 20 in the aorta 22. FIG. 3 is a partially cutaway sectional view of the invention disposed in place on the aorta 22 showing that at one end 24, the retention system 10a, shown partially in ghost lines, retains the graft 16 in the aorta 22, and the band 26 of the present invention, shown in sectional view, is disposed around the exterior of the aorta 22 at the location where the retention system 10a joins the graft 16 to the interior of the aorta 22. As a result of the positioning of the band 26, the aorta is supported and the graft 16 is secured in position. At the other end 25 of the graft 16, a second band 30 is shown in full form with the underlying retention system and graft shown in ghost lines. As can be seen, the band is sufficiently wide to carefully overlie the site where the retention system connects to the aorta, but not so wide so as to restrict the natural motion of the blood vessel in operation. It will also be appreciated by persons of skill in the art that the band can be of any width which will accomplish the intended purpose of supporting the blood vessel at the site of the connection between the graft and the blood vessel.

Figure 4:
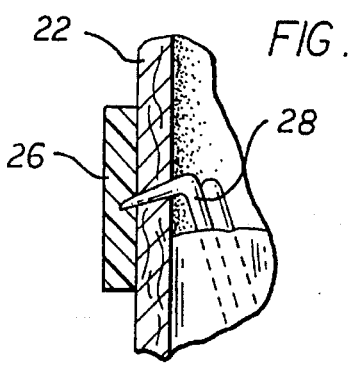
FIG. 4 is an enlarged view of a portion of the present invention disposed on a blood vessel with a retention system, taken through the section designated by the numeral 4 in FIG. 3.

FIG. 4 shows an enlarged view of the present invention strap 26 installed on a blood vessel 22 with a retention system 10a holding the graft 16 to the interior wall of the vessel 22. It will be appreciated that although in the present invention, the barb 28 is disposed entirely through the wall of the vessel 22, the barb 28 does not have to extend all the way therethrough in order for the present invention to function properly. While not being bound to any particular theory, the present invention functions by supporting the blood vessel and preventing it from expanding beyond its natural amount of expansion. It works like a girdle to provide the required support.

Figure 5:
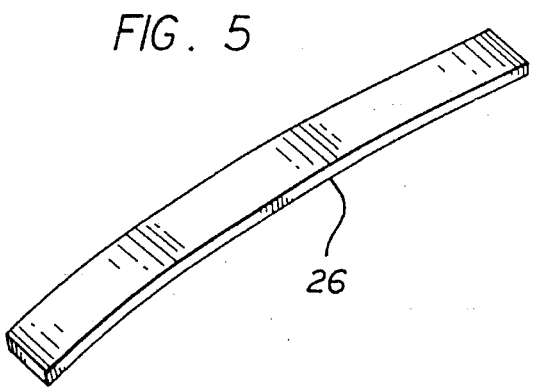
FIG. 5 is a perspective view of one embodiment of the strap of the present invention.

As shown in FIG. 5, one embodiment of the present invention is a strap that may be wrapped around a blood vessel to provide a snug fit, and then locked in place by any suitable means known in the art. Examples of suitable means are described in more detail below, but generally may including sewing, adhesives, melting using a cauterizing instrument or the like, hook and loop type fasteners, other bands or fasteners, snaps, belt buckles, friction type buckling systems, or other systems known in the art.

Figure 6:
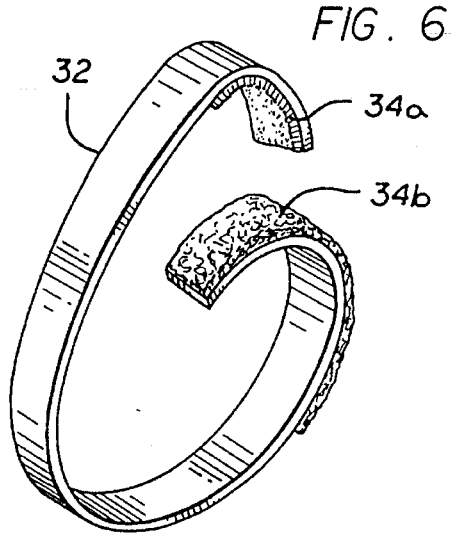
FIG. 6 is a perspective view of another embodiment of the present invention in a partially folded configuration.

As shown in FIG. 6, one embodiment of the present invention is disclosed in which the strap 32 is generally a fiat strap with mating hook and loop type fastening means (Velcro®) disposed on opposite sides of the strap so that they mate when the strap is folded into a circular configuration, and are used to lock the strap around a blood vessel. The hook and loop system, depicted by numerals 34a and 34b, are sufficiently long and disposed along a sufficient length of the strap 32 that the strap will have the desired length when closed around a blood vessel to provide the desired snug fit.

Figure 7:
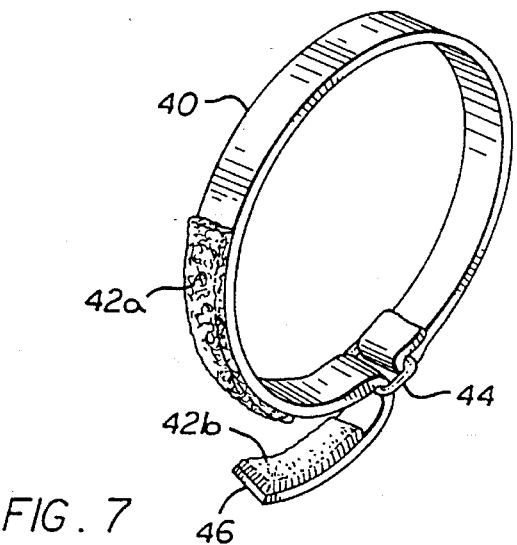
FIG. 7 is a perspective view of an alternative embodiment of the strap of the present invention.

As shown if FIG. 7, another embodiment of the present invention also utilizes a strap 40 with a hook and loop system, 42a and 42b disposed on the same side of the strap 40, and a buckle 44 through which end 46 of strap 40 is disposed, so that the strap 40 doubles back on itself and is locked in a closed circular configuration.

Figure 8:
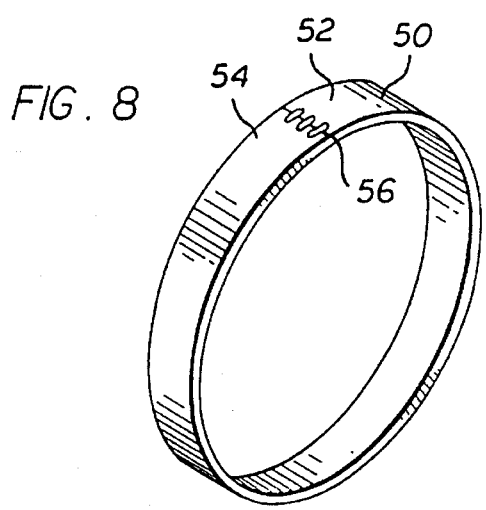
FIG. 8 is a perspective view of the another alternative embodiment of the strap of the present invention.

As shown in FIG. 8, in another embodiment of the present invention is a strap 50, similar to the form shown in FIG. 5, in which the ends 52 and 54 are sewn together with stitching 56.

Figure 9:
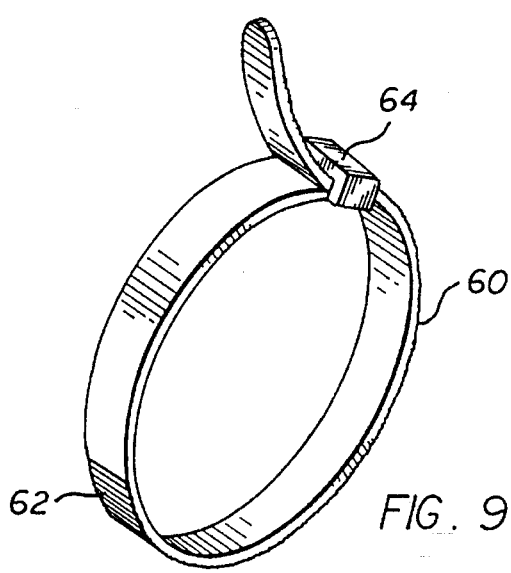
FIG. 9 is a perspective view of another alternative embodiment of the strap of the present invention.

As shown in FIG. 9, in another embodiment of the present invention is a strap 60 having a plurality of detents or ridges 62 on one surface and a buckle 64, like a cable tie buckle, which is known in the art, which locks the strap in a circular configuration when the end 66 is passed through the buckle 64 and pulled tight. This arrangement is advantageous because there are devices which can tighten such a strap to a desired tension, and such tensioning devices are already in use in medical, and particularly, surgical, applications. One example of such a tensioning device for these straps is a Panduit GS2B (Tinley Park, Ill.).

Figure 10:
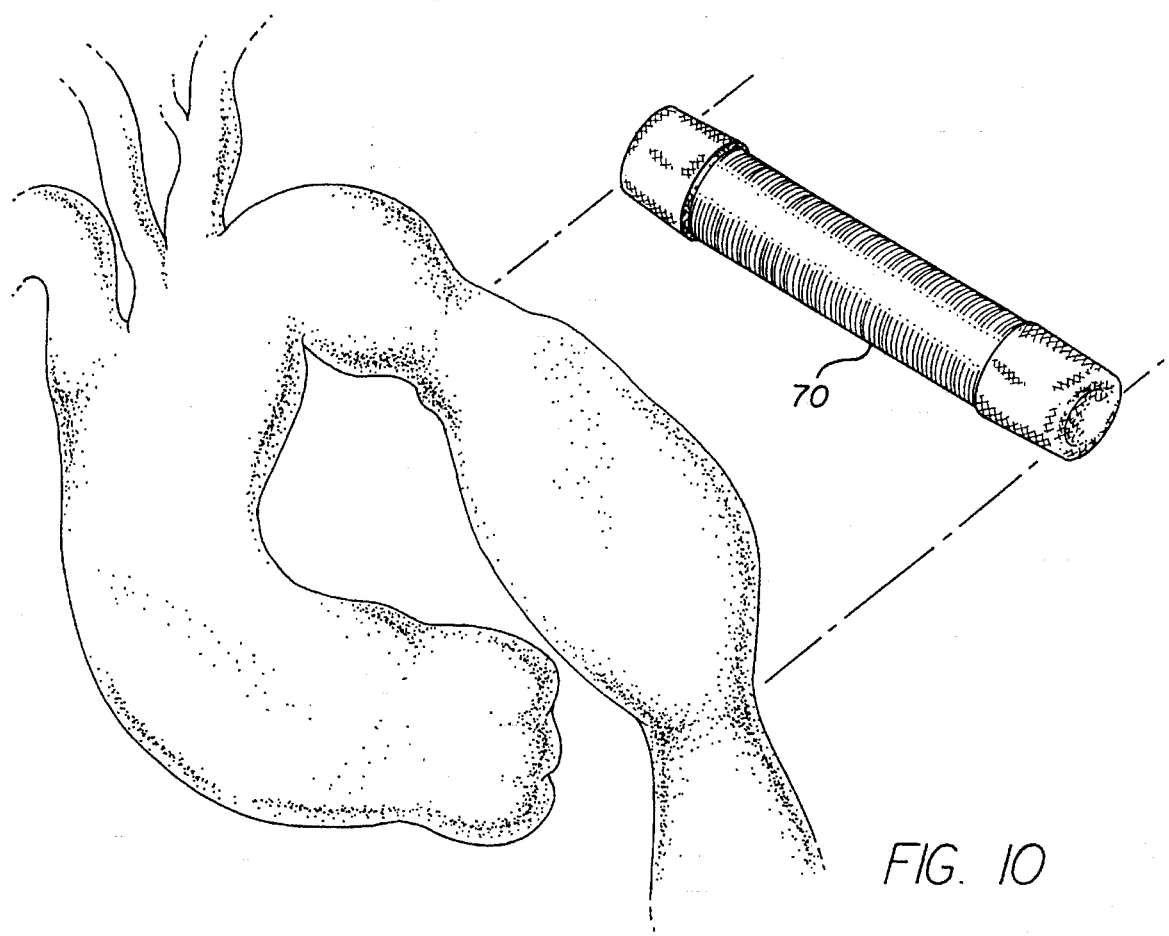
FIG. 10 is a perspective view of a prior art vascular graft.
Figure 11:
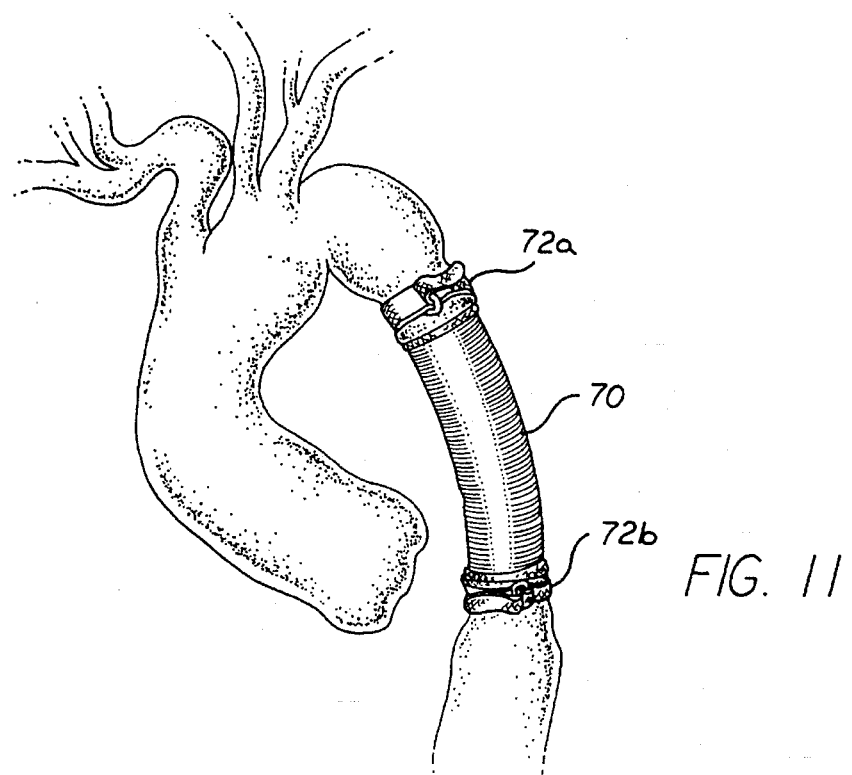
FIG. 11 is a perspective view of the present invention being used to retain a vascular graft.

As shown in FIGS. 10 and 11, the present invention can be used to secure an intraluminal vascular prosthesis or graft. A section of the aorta is shown with a dilated lumen as is known in the art. The graft 70, which is known in the art and can be obtained commercially from companies such as C. R. Bard, Inc., Vascular Systems Division, Billerica, Mass. The graft can be attached to the section of the aorta by means of the present invention 72a and 72b which is disposed within the walls of the lumen.

While the method and apparatus have been described in terms of various embodiments, other embodiments may come to mind to those skilled in the art without departing from the spirit and scope of the present invention. The invention should, therefore, be measured in terms of the claims which follow.

What I claim is:

1. An aortic graft assembly comprising:

a generally liquid impervious body having a first and second end, a graft retention system disposed at each of said first and second ends for attaching said graft to a blood vessel, a support strap adapted to surround the exterior of a blood vessel, said support strap having a closure means for retaining said strap in a circular configuration when said strap is disposed around the exterior of said blood vessel at a location adjacent to each of said graft retention systems.

2. The aortic graft assembly of claim 1 wherein said support strap comprises a closure means comprising a hook and loop fastener.

3. The aortic graft assembly of claim 1 wherein said support strap comprises a closure means comprising a loop to permit said support strap to double back on itself and a hook and loop type fastener on one side of said strap to secure said strap.

4. The aortic graft assembly of claim 1 wherein said support strap comprises a closure means comprising a suture.

5. The aortic graft assembly of claim 1 wherein said graft retention system comprises outwardly facing staples and said support strap is aligned with said staples.

6. The aortic graft assembly of claim 1 wherein said graft comprises a flexible, radially rigid tube, and said support strap couples said tube to two separated ends of a blood vessel.

7. In a vascular graft for resolving an aneurysm in a blood vessel of the type comprising a generally liquid impervious, tubular, collapsible and expandable body having a first and second end, and a graft retention system disposed at each of said first and second ends for attaching said graft to a blood vessel, in use, said graft retention system being collapsible and expandable, the improvement comprising a support strap adapted to surround the exterior of said blood vessel, said support strap having a closure means for retaining said strap in a circular configuration when said strap is disposed around a blood vessel at a location adjacent to each of said graft retention systems.

8. The support strap of claim 7, said support strap having a closure means comprising a hook and loop fastener.

9. The support strap of claim 7, said support strap having a closure means comprising a loop to permit said support strap to double back on itself and a hook and loop type fastener on one side of said support strap to secure said strap.

10. The support strap of claim 7, said support strap having a closure means comprising a suture.

11. A method of repairing an aneurytic blood vessel by inserting in said blood vessel at a location remote from the site of the aneurysm a vascular graft, positioning the graft at the site of the aneurysm, and securing said vascular graft to said blood vessel with a graft retention system, said graft retention system attaching to said blood vessel at positions on each side of said aneurysm, the improvement comprising securing around the exterior of said blood vessel at positions adjacent each of said graft retention systems, a strap wherein said strap does not penetrate said blood vessel.

12. The method of claim 11 wherein said strap is applied around said blood vessel at a predetermined tension.

13. The method of claim 12 wherein said strap is applied around said blood vessel at a predetermined tension by an adjustable tension gauge device.

14. The method of claim 12 wherein said strap is secured around said blood vessel by a strap retention means comprising a suture.

15. The method of claim 12 wherein said strap is secured around said blood vessel by a strap retention means comprising a hook and loop type fastener.

16. The method of claim 12 wherein said support strap comprises a closure means comprising a loop to permit said support strap to double back on itself and a hook and loop type fastener on one side of said strap to secure said strap.

17. The method of claim 12 wherein said support strap is closed by heating said support strap to heat weld it to itself.

* * * * *